United States Patent
Lou et al.

(10) Patent No.: US 8,528,582 B2
(45) Date of Patent: Sep. 10, 2013

(54) METHOD OF CHANGING FLUID FLOW BY USING AN OPTICAL BEAM

(75) Inventors: Janet W. Lou, Springfield, VA (US); Carl A. Villarruel, Burke, VA (US); Ross Schermer, Springfield, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/457,140

(22) Filed: Apr. 26, 2012

(65) Prior Publication Data

US 2012/0273054 A1 Nov. 1, 2012

Related U.S. Application Data

(60) Provisional application No. 61/479,906, filed on Apr. 28, 2011.

(51) Int. Cl.
*F15C 1/04* (2006.01)

(52) U.S. Cl.
USPC ............................. 137/13; 137/806; 137/828

(58) Field of Classification Search
USPC ............................. 137/13, 806, 825, 827, 828
See application file for complete search history.

(56) References Cited

U.S. PATENT DOCUMENTS

| 4,893,886 | A | 1/1990 | Ashkin et al. |
| 7,204,263 | B2 * | 4/2007 | Tsukita et al. ............... 137/2 |
| 2002/0122618 | A1 | 9/2002 | Kim |
| 2002/0176069 | A1 | 11/2002 | Hansen et al. |
| 2002/0181837 | A1 | 12/2002 | Wang et al. |
| 2005/0207940 | A1 | 9/2005 | Butler et al. |
| 2009/0090422 | A1 * | 4/2009 | Baroud et al. ................ 137/827 |
| 2009/0114285 | A1 * | 5/2009 | Hashimoto et al. ............. 137/13 |
| 2009/0178716 | A1 * | 7/2009 | Kaduchak et al. .............. 137/13 |
| 2009/0283148 | A1 * | 11/2009 | Shinoda et al. .................. 137/2 |
| 2009/0308473 | A1 * | 12/2009 | Shinoda ........................ 137/827 |

OTHER PUBLICATIONS

R. Piazza, "Thermophoresis: moving particles with thermal gradients", Soft Matter, vol. 4, pp. 1740-1744, 2008.

S. B. Kim and S. S. Kim, "Radiation forces on spheres in loosely focused Gaussian beam: ray-optics regime", J. Opt. Soc. Amer. B, vol. 23, pp. 897-903, 2006.

B. Selva, V. Miralles, I. Cantat, and M.-C. Jullien, "Thermocapillary actuation by optimized resister pattern: bubbles and droplets displacing, switching, and trapping", Lab on a Chip, vol. 10, pp. 1835-1840, 2010.

Y.-F. Yap, S.-H. Tan, N.-T. Nguyen, S. M. S. Murshed, T.-N. Wong, and L. Yobas, "Thermally mediated control of liquid microdroplets at a bifurcation", J. Phys. D: Appl. Phys., vol. 42, 065503, 2009.

* cited by examiner

*Primary Examiner* — Craig Schneider
(74) *Attorney, Agent, or Firm* — Amy Ressing; Roy Roberts (57) ABSTRACT

The application of an optical beam redirects sheathed microfluidic flow without direct interaction with the sample. The hydrodynamic properties of the sheath are locally modified due to optical absorption and heating, resulting in a spatial shift of the sample flow. The technique can result in up to 100 μm shift at peak flow velocities of 19 mm/sec.

17 Claims, 6 Drawing Sheets

METHOD OF CHANGING FLUID FLOW BY USING AN OPTICAL BEAM

CROSS-REFERENCE TO RELATED APPLICATIONS

This Application claims the benefit of U.S. Provisional Application 61/479,906 filed on Apr. 28, 2011.

BACKGROUND

Laminar flow, including sheath flow, is a technique useful in a variety of applications, including bead/particle counting, flow cytometry, waveguiding, liquid chromatography, fluorescence measurements, and other biological and chemical analyses. Sheath flow involves surrounding a central flow stream (the core) with a surrounding stream (the sheath), wherein fluidic (e.g., hydrodynamic) forces compress the core flow stream into a narrow region. This permits the counting, detection, and/or sorting of a sample in the core, such as particles, beads, cells, and the like. In particle counting and flow cytometry applications, the sheath prevents particles in the core from coming into contact with the walls of the channel, thus preventing adhesion and clogging. The sheath also serves to focus the particles or molecules into the center of the channel, allowing for easy counting or measurement through optical or other means.

Sheath flow is a type of laminar flow where a sheath stream surrounds a core stream, with substantial avoidance of mixing between the core stream and the sheath stream. Laminar flow can also be used with fluids of different refractive index to create a waveguide in the core or sheath stream in order to measure transfer of analytes from one stream to the other, or to control the rate of interaction between molecules in one or both streams for carefully controlled chemistry or analysis.

Two-dimensional ("2D") flow focusing uses sheath flow to horizontally compress a sample flow towards the center of a flow cell or channel. With such an approach, the spatial particle/bead distribution within the flow remains unaffected in the third dimension, normally vertically. Three-dimensional ("3D") flow focusing controls particle spatial distribution in the vertical dimension as well, by further focusing the sample flow in the vertical direction with three-dimensional sheathed flow, with the core stream surrounded on all sides.

For "Lab-On-A-Chip" applications, a well defined and dimensionally stable narrow particle/bead flow stream is very desirable. Additionally, three-dimensional sheathed flow (also termed 3D fluidic focusing) mitigates wall flow effects and sample damage, and reduces detection errors due to multiple particle events.

It is desirable to control the path of fluidic flow. One method of redirecting the sample flow is physical, such as closing a valve to the undesired path(s) and opening a valve to the desired path. However, with microfluidic flow, such mechanical systems would need to be extremely small and therefore, prone to damage, and may cause flow instabilities during the transient times when opening and closing. Additionally, they are often slow (response time >100 ms) and may require physical contact with the sample flow. A need exists for an improved method for controlling microfluidic flow.

BRIEF SUMMARY

In one embodiment, a method of directing focused flow includes providing a focused flow comprising a core stream positioned in a sheath flow, and applying an optical beam upon the sheath flow, thereby heating the sheath flow, whereby the heating cases a shift of the position of the core stream in the focused flow.

In a further embodiment, method of directing focused flow includes providing a focused flow comprising a core stream positioned in a sheath flow inside an apparatus; applying an infrared laser upon the sheath flow, thereby heating the sheath flow; and modulating the amplitude of the infrared laser and/or applying the infrared laser at more than one position, thereby shifting the position of the core stream to transit a selected output port of the apparatus.

In another embodiment, an apparatus includes a channel operably connected to at least one inlet port and a plurality of outlet ports and a source of an optical beam, wherein the apparatus is adapted to direct the optical beam at a sheath flow portion of a fluidic flow in the channel while modulating the amplitude of the optical beam and/or applying the optical beam at more than one position, thereby directing a core stream portion of the fluidic flow at a selected output port.

BRIEF DESCRIPTION OF THE DRAWINGS

FIG. 1 shows cross-sectional schematics of 2D and 3D flow.

FIG. 3 shows schematic drawings of the micro-fluidic cells used in demonstrations. FIG. 4 shows half-maximum edge locations of the core flow, with and without the presence of an optical beam (namely a 1480 nm laser).

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

As used herein, "focused flow" refers to a type of laminar flow where a core stream is contained by sheath flow in either two or three dimensions, so mixing between the core stream and the sheath flow is substantially avoided.

Description

Figure 1A:
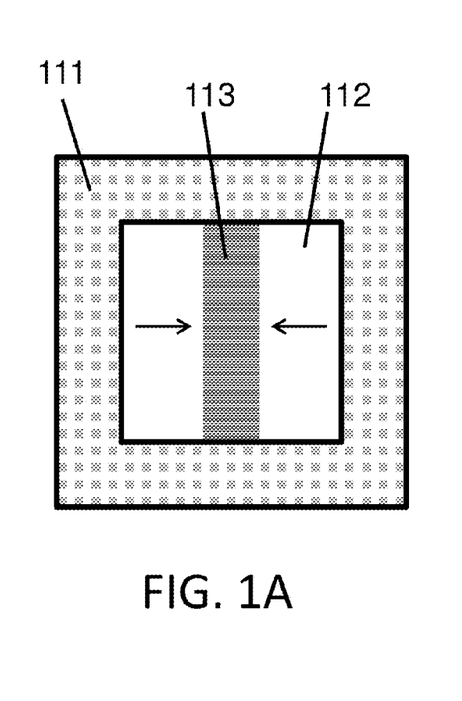
FIG. 1A illustrates 2D flow.
Figure 1B:
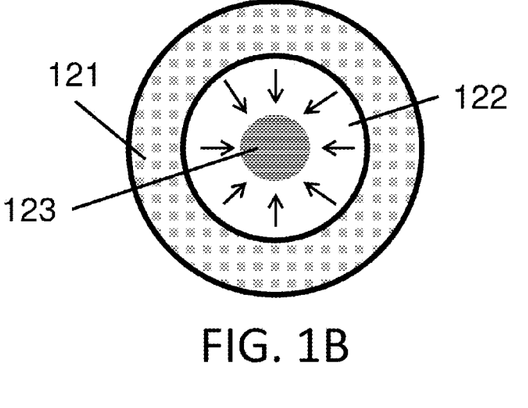
FIG. 1B illustrates 3D flow in a round channel.
Figure 1C:
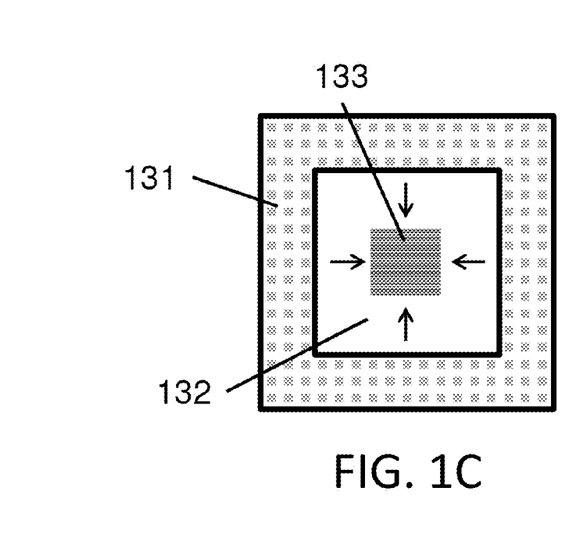
FIG. 1C illustrates 3D flow in a channel with a square cross section.

FIG. 1 shows cross-sectional schematics of 2D and 3D focused flow. FIG. 1A illustrates 2D flow, FIG. 1B illustrates 3D flow in a round channel, and FIG. 1C illustrates 3D flow in a channel with a square cross section. The channels 111, 121, 131 contain the focused flow, which comprises the respective core streams 113, 123, 133 and sheath streams 113, 123, 133. The sheath exerts inward force on the core as shown by the arrows in each figure.

As noted above, using mechanical means to control fluidic flow offers several disadvantages.

Changing the sheath flow rate on one side of the core relative to the sheath flow rate on the other side of the core will alter the position of the core within the micro-fluidic channel. However, this technique is subject to various disadvantages. When the fluidic flows are pressure-driven (such as when the flow is supplied using one or more syringes), any change in the pressure is relatively slow compared to the sample flow rate, since any change in the drive pressure must propagate through the fluidic system. For example, if the pressure change has a response time of 1 s, a sample flowing at 10 mm/s would have traveled 10 mm, which is often the entire length of the fluidic device. Furthermore, the pressure changes continue to propagate beyond the location of the sample and therefore, the effect cannot be localized to a segment of the sample flow.

Electrokinetic effects and magnetophoresis are both known methods of "switching" the path of particles in a fluid flow. Electrokinetic effects include electrophoresis, electroosmosis, sedimentation potential, and streaming potential (see Reference 1). The basis of these effects is that a charged surface or particle will move relative to an uncharged surface or particle due to an applied electric field. In order to create a strong force to achieve significant movement, the product of the mobility and the electric field must be high. Often times, this means that high voltages, on the order of kV, would be necessary. In the case of magnetophoresis, the particles must have either an induced or permanent magnetization in order for an applied magnetic field to affect the path of the particle (see Reference 2). This limits the applicability of the technique to certain types of paramagnetic or magnetic particles, and thus undesirably excludes numerous applications, such as those on biological cells.

Thermal gradients have been used to shift beads (see Reference 3), bubbles, and droplets (see References 4 and 5). The principle is based on the fact that heating changes the surface tension of the liquid surrounding the bead/bubble, thereby changing its equilibrium position. In most cases, this technique does not operate on the fluid itself and is highly dependent on the surface tension which may vary for different bead materials and sizes. The exception is in the case of droplets. However, the flow velocities required for the successful application of this technique to droplets are very low, on the order of μl/hr (see Reference 4). Other techniques create thermal gradients by means that are external to the micro-fluidic flow and rely on thermal conduction to bring the thermal changes into the flow channel. This can be very slow since the heat must first propagate through the surrounding material before reaching the flow. In contrast, the technique described herein directly heats the flow using an optical beam, and as a result the heating is practically instantaneous.

Previous work involving direct, localized optical interaction with the core via radiation pressure has been demonstrated, but this approach suffers from various disadvantages. First, it is necessary to use an optical beam that is approximately the same size as the core. For larger cores, this means a larger beam is required. This, in turn, reduces the optical power density and affects the amount of interaction that can be achieved. Additionally, it is necessary to project the optical beam to the location of the core in the micro-fluidic channel. This can be particularly challenging since it means that a precise beam size must be achieved at a location with a precision on the order of microns. Optical absorption is also a problem when using this technique, since absorption can lead to undesirable heating of a sample that is often located in the core stream, which can damage the sample. Cross-type bead sorting with an optical beam has been demonstrated, but the optical force that can be exerted is low (see Reference 6). According to Reference 7, a 100 μm shift can be achieved only at low flow velocities (100 m/sec).

As described herein, applying an optical beam so that (preferably most of) the energy therein is directed upon the sheath flow allows for controlling the position of the core flow while overcoming the above-described disadvantages. Optical heating changes the hydrodynamic properties of one side of the sheath flow, thereby changing the relative sheath flow rates on either side of the core. This causes the core location to shift position within the micro-fluidic channel. Because the sheath fluid is flowing in the channel with the sample fluid, the heating of the fluid only alters the position of the core adjacent to the heated area. The heated sheath and shifted core continue to propagate together down the micro-fluidic channel until the heat dissipates from the sheath, as noted in detail below with regard to FIG. 5.

Figure 2:
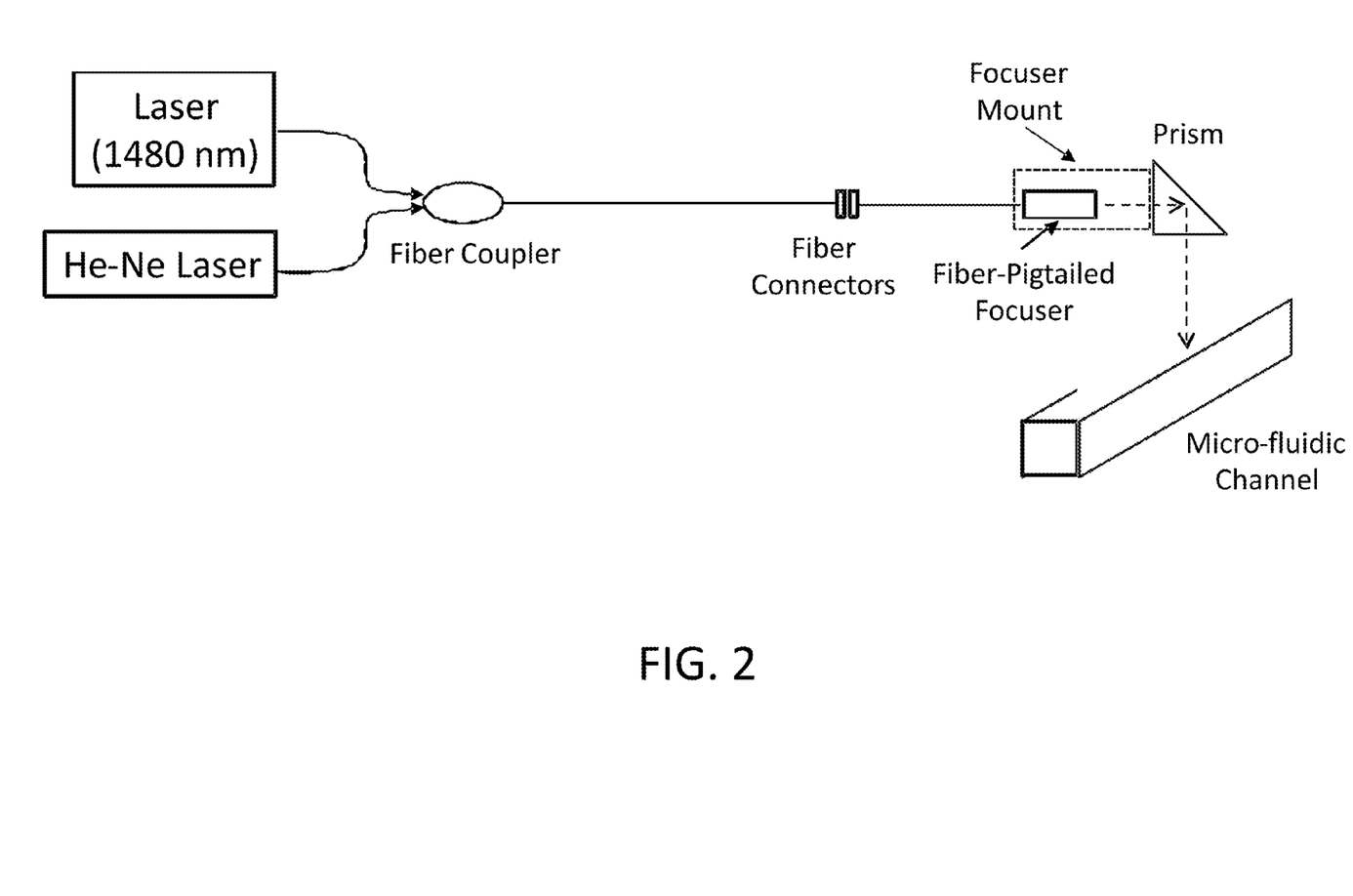
FIG. 2 is a schematic diagram of an exemplary arrangement of the described technique. The dashed arrows indicate the optical beam path.

FIG. 2 shows a schematic diagram of an exemplary arrangement for conducting the described technique. The dashed arrows indicate the optical beam path. The laser source is a fiber-pigtailed, 1480 nm wavelength, laser diode. The laser output is connected to a fiber coupler, and the output is connected to an optical focuser. Also connected to the fiber coupler is a HeNe laser. The HeNe laser allows visualization of the position of the optical beam, and is not required for operation. Naturally, the fiber coupler can be omitted if only one laser source is used. The output of the focuser is measured to have a minimum focal spot of ~68 μm at a distance of ~32 mm. A right angle prism is attached to the focuser mount to redirect the optical beam to be orthogonal to the direction of flow.

Figure 3A:
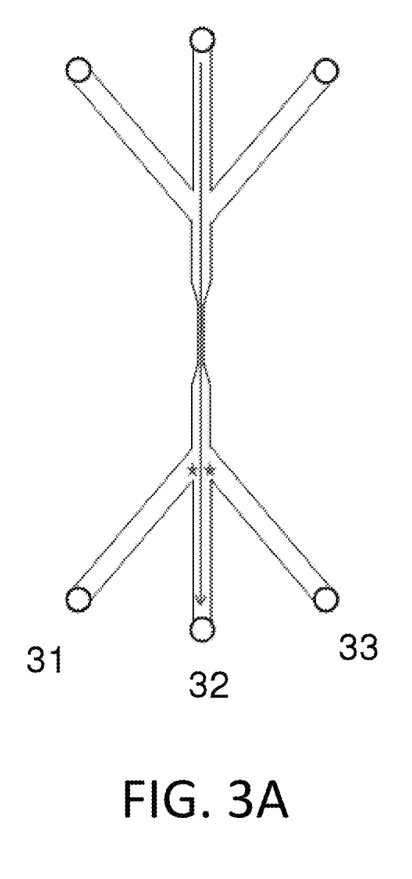
FIG. 3A shows device D1, constructed of plastic.
Figure 3B:
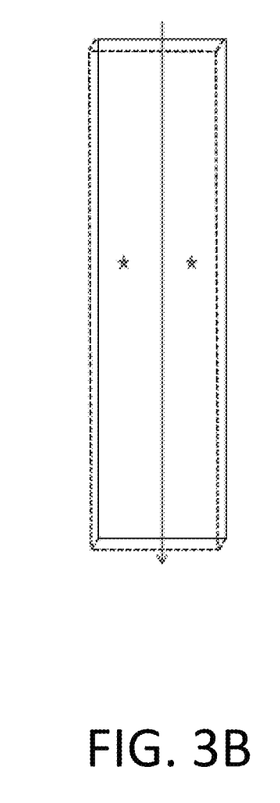
FIG. 3B shows device D2, constructed of silica glass. The stars indicate two possible locations for the optical beam. The arrows show the direction of sample fluidic flow

This technique was demonstrated in two different microfluidic configurations, seen schematically in FIG. 3. The stars indicate two possible exemplary locations for the optical beam. The arrows show the direction of fluidic flow. The micro-fluidic device termed D1 shown in FIG. 3A is made of plastic and has two sheath input ports and one sample input port, at the top of the figure. The flow focusing results in a sample flow that is compressed by the sheath flow for 2D flow focusing and occupies only a fraction of the width of the micro-fluidic channel, however, the sample flow is unaffected by the sheath flow in the orthogonal direction and occupies the entire height of the micro-fluidic channel (see FIG. 1A). The second micro-fluidic device, termed D2 and shown schematically in FIG. 3B, is made of fused silica and has eight sheath input ports and one sample input port. The sheath inputs are arranged such that the sheath completely surrounds the sample and thus, accomplishes 3D flow focusing, wherein the sample flow occupies a fraction of both the height and width of the micro-fluidic channel. For both devices, the optical beam is directed into the sheath flow on one side of the sample flow and is adjacent to the sample flow, at the points identified with stars in FIG. 3. The fluidic flow was found to remain intact, with separate core and sheath, at the point of application of the optical beam and downstream thereof.

In one embodiment, it is contemplated that application of the optical beam may cause the core to shift to various output ports. For example, in FIG. 3A, the core would flow to output port 32 in the absence of the optical beam, while application of the optical beam at either of the starred locations may shift the output to the output port 31 or 33 that is laterally opposed to the beam. This can be accomplished in various ways including using two optical beams (one directed at each of the starred locations) and modulating their amplitude (including simply switching them on and off), or aiming a single beam at either aim point using, for example a reflector or prism. This could be extended to 3D focused flow with a core shifting in two dimensions The micro-fluidic device may be made of other materials, have other configurations, and/or use other fluids, however it should have at least one portion that is substantially transparent to the optical beam to allow the beam to contact the sheath flow. It is preferable to reduce absorption in the device to the greatest extent possible to avoid heat generation outside the fluidic flow. Flow focusing can also be accomplished using techniques described in commonly-owned U.S. patent application Ser. No. 13/309,830, filed Dec. 2, 2011.

In device D1, the fluidic channel at the location of application of the optical beam is 2 mm wide and 150 μm in height. In device D2, the channel is a tube with ~492 μm×492 μm inner dimensions. The optical beam is directed into the sheath flow on one side of the core. The heating of the sheath is preferably highly localized, so that only the core adjacent to the heated area is shifted.

The presence of the optical beam causes the core to shift its location within the channel towards the heated side. Shifts of up to 100 μm were seen at peak flow velocities ($v_{pk}$) of ~19 mm/s (total volume flow rates of 220 μL/min). FIG. 3 shows half-maximum edge locations of the core flow, with and without the presence of an optical beam (namely a 1480 nm laser). FIG. 3A is for device D1 and FIG. 3B is for device D2. The half-maximum edge locations are plotted as a function of the distance along the channel. The amount of shift is proportional to the flow rate (i.e., the duration of time the segment of water is heated by the optical beam).

Figure 4A:
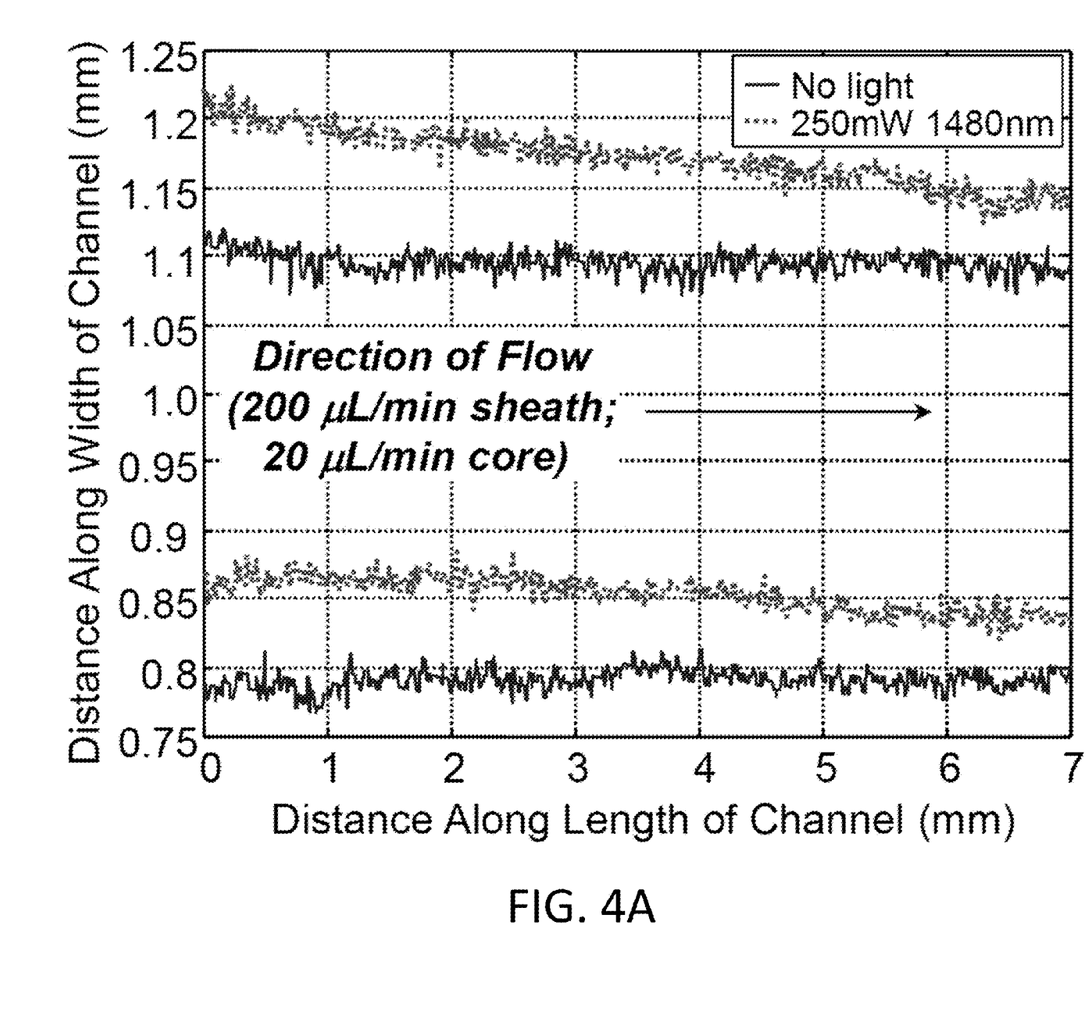
FIG. 4A is for device D1 and FIG. 4B is for device D2.

For device D1 (data shown in FIG. 4A), up to 100 μm shift was obtained for $v_{pk}$ of about 19 mm/s (average flow velocity ($v_{avg}$) about 12 mm/s). The core position returned to its original position after some distance (time), which corresponds well to the heat relaxation time constant. Core shifting was measured for a range of flow rates, and even greater shifts were seen at slower velocities.

Figure 4B:
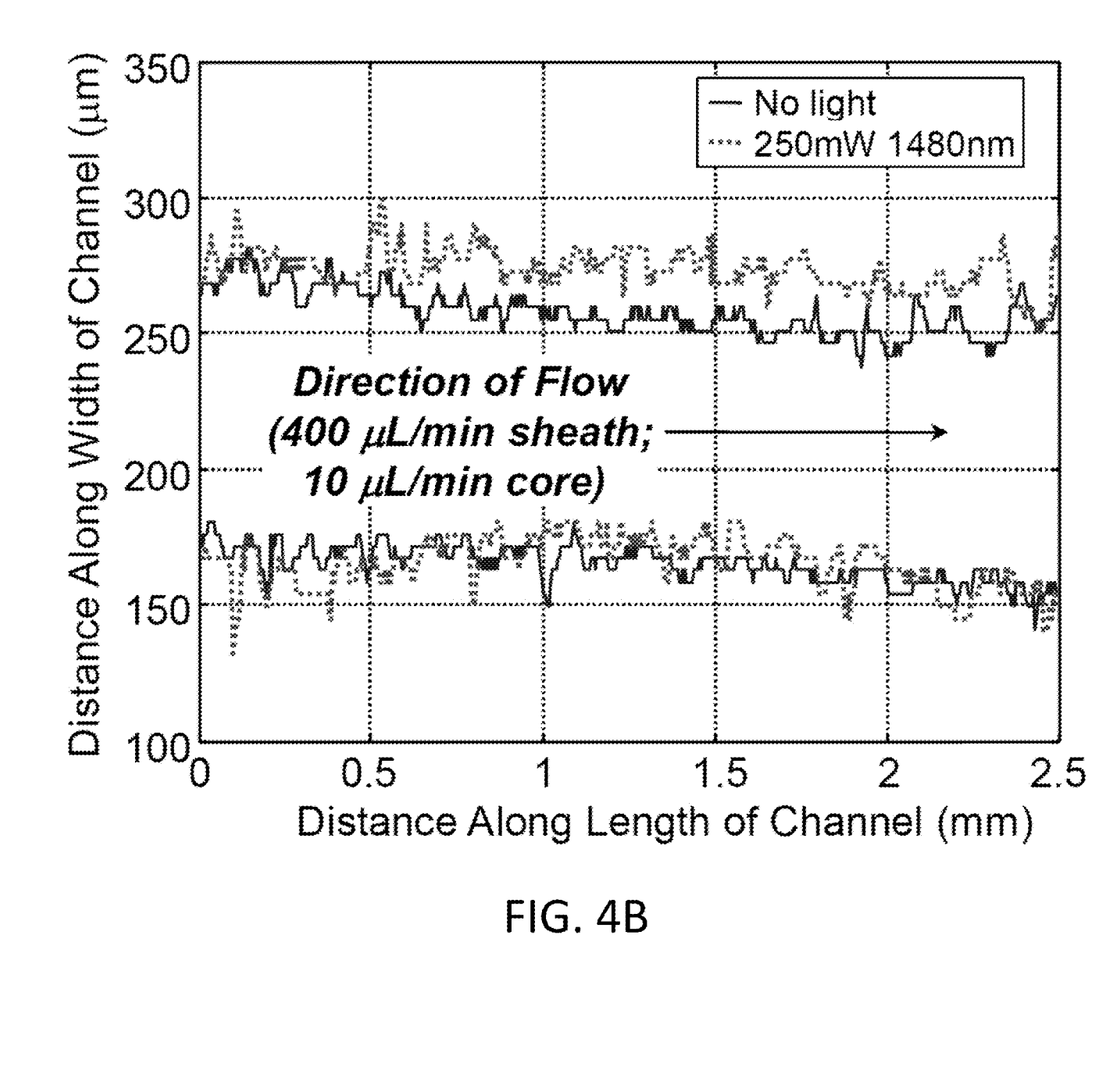

FIG. 4B plots the edges of the core in D2 as a function of distance along the micro-fluidic channel. About a 12 μm shift was obtained for >2 times the flow velocity compared to that in FIG. 4A ($v_{pk}$ of about 59 mm/s, $v_{avg}$ about 28 mm/s). It is noted that the depth of fluid that the optical beam must heat in D2 is >3 times that in D1. Thus, for the same optical power, the heat induced displacement is expected to be about 7 times lower, and results obtained are consistent with that expectation.

The data in FIG. 4 was obtained using an optical power of ~250 mW. This technique is expected to function at lower optical power and at lower power density. The use of higher power levels was found to correspond to greater shifts in the core, and higher power densities correspond to faster response times. Analog as well as digital modulation has been impressed to the optical beam intensities, resulting in corresponding modulations in the shifts of the core.

The optical beam is most preferably a laser, however other forms of focused light can be used. The fluid to be heated should have some optical absorption at the (peak) wavelength of the optical beam.

The focuser is used to ensure that the optical power is concentrated into a location in the sheath flow, adjacent to the sample flow, but not into the actual sample flow itself. Depending on the micro-fluidic channel geometry and dimensions, other focusers or beam size modifiers may be used to achieve other spot sizes.

The prism is used simply to redirect the optical beam. It is possible to use another suitable optical element as a reflector to direct the beam. In an embodiment, an optical element directs the optical beam to more than one location. Alternatively, no reflector would be needed if the optical focuser could be aligned such that the direct beam can be used for actuating the sample flow shift. It is also possible to use more than one optical beam.

Changing the spot size of the optical beam will cause the heating to occur at different rates. The smaller beams will heat the sheath flow faster. The heating rate is directly related to the overall switching response time of the system. Laser-induced thermal effects can be observed at modulation rates of at least 10 kHz (i.e., <100 μs), which is much faster than previously described modulation of microfluidic flow. In an embodiment, a controller directs the modulation and/or aiming of the optical beam.

It is contemplated that the shift induced by the optical beam may be used to direct the core to a selected path for sorting, analysis, collection, and/or processing, and the like. This has been at least partially accomplished to date.

Figure 5:
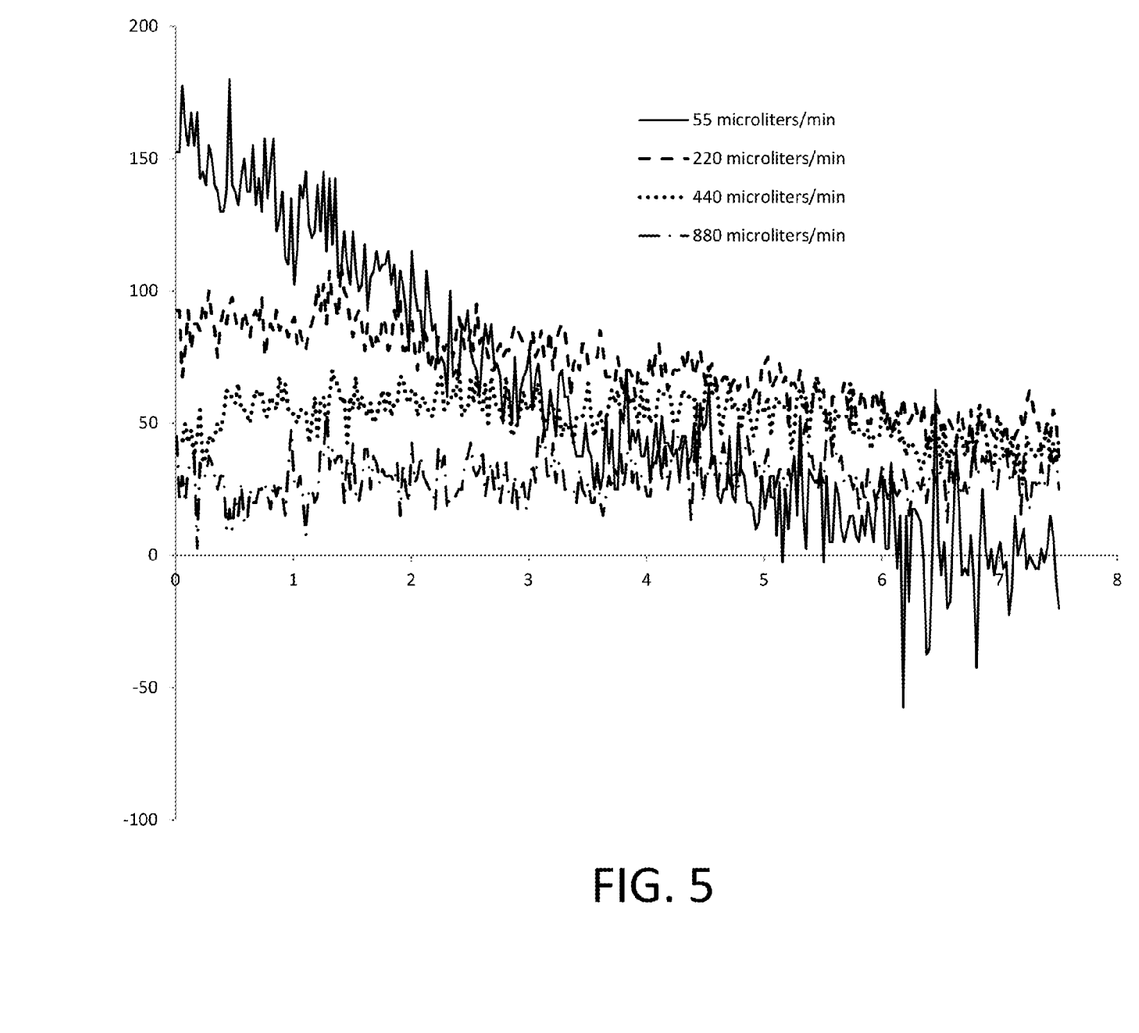
FIG. 5 displays data showing the displacement of a shifted core downstream of the optical beam as a function of distance along the channel, for different flow rates.

FIG. 5 displays data showing the displacement of a shifted core downstream of the optical beam as a function of distance along the channel, for different flow rates. The X axis is distance downstream of the optical beam, in mm. The Y axis is the lateral displacement of the core in microns. It can be seen that the core tends to return to its original position as it flows downstream, and that the lateral displacement is greatest at lower flow rates.

Advantages

This technique allows one to achieve large shifts in the location of the sample flow at high flow rates, without directly interacting with the sample fluid. Furthermore, because heating of the fluid only alters the position of the core adjacent to the heated area, the "upstream" nor "downstream" core/sheath flows are affected.

Because the optical beam originates outside the physical device, there are many manufacturing and construction advantages. First, the location where the shift is actuated can be changed by simply changing the location where the optical beam heats the sheath flow. More precisely, the focus of the optical beam where the greatest heating takes place can be translated along the length of the channel as well as along the height of the channel. In the case of 3D flow focusing, the sample flow may be shifted both up/down as well as sideways, simultaneously. Thus, the system is highly reconfigurable. Second, there are no physical components that need to be added to the flow channel. This avoids potential problems with clogging in the flow channels.

REFERENCES

[1] H. Bruus, Theoretical Microfluidics, Oxford Univ. Press: New York, p. 143, 2009.
[2] Id., p.187.

[3] R. Piazza, "Thermophoresis: moving particles with thermal gradients", Soft Matter, vol. 4, pp.1740-1744, 2008.

[4] Y.-F. Yap, S.-H. Tan, N.-T. Nguyen, S. M. S. Murshed, T.-N. Wong, and L. Yobas, "Thermally mediated control of liquid microdroplets at a bifurcation", J. Phys. D: Appl. Phys., vol. 42, 065503, 2009.

[5] B. Selva, V. Miralles, I. Cantat, and M.-C. Jullien, "Thermocapillary actuation by optimized resister pattern: bubbles and droplets displacing, switching, and trapping", Lab on a Chip, vol. 10, pp.1835-1840, 2010.

[6] S. B. Kim and S. S. Kim, "Radiation forces on spheres in loosely focused Gaussian beam: ray-optics regime", J. Opt. Soc. Amer. B, vol. 23, pp.897-903, 2006.

[7] S. B. Kim, J. H. Kim, and S. S. Kim, "Theoretical development of in situ optical particle separator: cross-type optical chromatography", Appl. Opt., vol. 45, pp.6919-6924, 2006

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. A method of directing focused flow, the method comprising:
   providing a focused flow comprising a core stream positioned in a sheath flow, and
   applying an optical beam upon the sheath flow, thereby heating the sheath flow,
   whereby the heating causes a shift of the position of the core stream in the focused flow,
   wherein the sheath flow absorbs a majority of the energy in the optical beam.

2. The method of claim 1, wherein the core flow is not contacted by the optical beam.

3. The method of claim 1, further comprising modulating the amplitude of the optical beam and/or applying the optical beam at more than one position.

4. The method of claim 1, wherein more than one optical beam is applied at the sheath flow.

5. The method of claim 1, wherein the optical beam is focused to a diameter of less than 100 μm.

6. The method of claim 1, where in the optical beam is obtained from a laser.

7. The method of claim 6, wherein said laser emits infrared light.

8. The method of claim 1, wherein the focused flow is in a channel with a diameter of no greater than 5 mm.

9. The method of claim 1, wherein the focused flow is in a channel with a diameter of no greater than 10 mm.

10. The method of claim 1, wherein the focused flow is in a channel with a shortest dimension of no greater than 250 μm.

11. The method of claim 1, wherein the core is shifted at least 50 microns.

12. The method of claim 1, wherein the focused flow has a velocity of at least 100 μm/sec.

13. The method of claim 1, wherein the position of the core stream is shifted by 100 μm or greater at a peak flow velocity of 19 mm/s.

14. The method of claim 1, wherein the shift of the position of the core stream causes the core stream to transit a selected output port.

15. A method of directing focused flow, the method comprising:
    providing a focused flow comprising a core stream positioned in a sheath flow inside an apparatus;
    applying an infrared laser upon the sheath flow, thereby heating the sheath flow; and
    modulating the amplitude of the infrared laser and/or applying the infrared laser at more than one position, thereby shifting the position of the core stream to transit a selected output port of the apparatus
    wherein the sheath flow absorbs a majority of the energy in the optical beam.

16. An apparatus for directing focused flow, the apparatus comprising:
    a channel operably connected to at least one inlet port and a plurality of outlet ports and
    a source of an optical beam,
    wherein the apparatus is adapted to direct the optical beam at a sheath flow portion of a fluidic flow in the channel while modulating the amplitude of the optical beam and/or applying the optical beam at more than one position, thereby directing a core stream portion of the fluidic flow at a selected output port
    wherein the sheath flow absorbs a majority of the energy in the optical beam.

17. The apparatus of claim 16, wherein the source of the optical beam is an infrared laser.

* * * * *